United States Patent [19]

Erbeia

[11] 4,178,695
[45] Dec. 18, 1979

[54] NEW PROCESS FOR PREPARING PHARMACEUTICAL, COSMETIC OR DIAGNOSTIC FORMULATIONS

[76] Inventor: Angélo Erbeia, 6 rue René Blanc, 74100 Annemasse, France

[21] Appl. No.: 875,542

[22] Filed: Feb. 6, 1978

[30] Foreign Application Priority Data

Sep. 19, 1977 [FR] France .................. 77 28193

[51] Int. Cl.$^2$ .................................. F26B 5/06
[52] U.S. Cl. .................................. 34/5; 34/13
[58] Field of Search ..................... 34/5, 13

[56] References Cited

U.S. PATENT DOCUMENTS 3,309,779  3/1967  Ginnette et al. .................. 34/5

Primary Examiner—John J. Camby
Attorney, Agent, or Firm—Young & Thompson

[57] ABSTRACT

The process produces pharmaceutical, cosmetic or diagnostic formulations by the freeze drying of one or more substances in solution or in suspension in a solvent or a mixture of solvents. The solution or suspension is locally and progressively cooled in a controlled manner while agitating so as to produce microcrystals of solvent which are put in suspension in the remainder of the liquid until there is obtained a high-viscosity microcrystalline complex system comprising essentially isolated microcrystals of solvent in intimate mixture with interstitial liquid phases having a high concentration of the initially present substances. The microcrystalline complex system is hardened by cooling and lyophilized. This process permits the obtainment of lyophilized formulations having a higher dissolving or dispersing rate and lyophilized compositions of normally incompatible substances.

20 Claims, No Drawings

NEW PROCESS FOR PREPARING PHARMACEUTICAL, COSMETIC OR DIAGNOSTIC FORMULATIONS

The present invention relates to a process for preparing pharmaceutical, cosmetic or diagnostic formulations by freeze drying of substances in solution or in suspension in a solvent or a mixture of appropriate solvents, capable of permitting the lyophilization of associations of products which was heretofore impossible to produce and improving the performances of this technique.

It is known that many of the natural substances and many synthetic products are unstable in a liquid medium and must be treated by freeze drying in order to ensure that they are preserved for a suitable period.

It is known that the freeze drying or cryodesiccation comprises putting into solution in an appropriate solvent, most usually water, one or more active principles to which there may or may not be added excipients or adjuvents, freezing the solution obtained and eliminating the solvent by sublimation preferably under low pressure and at a sufficiently low temperature to avoid causing damage to the products initially put into solution, it being necessary to carry out the whole of the operation from the rigid state in accordance with a cycle particular to each case.

The lyophilization has permitted the obtainment of dehydrated products or products from which the solvate has been removed which keep well and are easily re-hydrated which permits a generally very rapid dissolving or putting into suspension.

On the other hand, for the preparation of pharmaceutical, cosmetic or diagnostic formulations, two or more substances must often be united, but it is difficult and even impossible to achieve this when a physical or chemical incompatibility exists between the substances.

The process according to the present invention has for purpose to considerably increase the possibilities and the field of application of lyophilization, in particular to permit the production of mixtures of substances which are normally incompatible in solution and permit the perfect mixture with the lyophilizate of powdered, crystalline, granulated substances which may or may not be coated, without the addition of substances other than those of which the product is normally composed. It moreover permits enhancing the advantages of lyophilization and mainly obtaining higher dissolving or dispersing rates.

The present invention provides a process comprising locally and progressively cooling in a controlled manner while agitating a solution or a suspension of an active principle or of a mixture of active principles in a solvent or a mixture of solvents to which excipients may or may not be added, so as to produce microcrystals of solvent from the liquid phase, continuously putting the microcrystals in suspension in the remaining liquid until the obtainment of a microcrystalline complex system having a high viscosity consisting essentially of isolated microcrystals of solvent in an intimate mixture with interstitial liquid phases having a high concentration of active principles and any possible carrier substances which were initially present.

This microcrystalline complex system may be obtained in particular by a progressive and controlled localized cooling of the solution, by injection of freezing or cryogenic fluid in a liquid mass subjected to agitation.

It is also possible to obtain microcrystals by a progressive and controlled localized cooling in a vessel the cooled surface of which is scraped. Known examples of such apparatus are freeze-concentration apparatus.

The typical properties and structures of a cold microcrystalline complex system depend on the solvent employed, the nature and concentration of the dissolved substance or substances and the manner in which the microcrystals are formed.

In particular, it is possible to increase the fineness of the microcrystals, in particular by increasing the rate of agitation, moderating the rate of cooling and increasing the speed of the scraping blade if such an apparatus is employed.

Depending on each case, the equipment employed may comprise one or more crystallizers and operates in a continuous or discontinuous manner with individualized batches.

The microcrystalline complex system having high viscosity thus obtained may be divided into particles by means of an adapted nozzle or distributed, by plastic flow, pressure, moulding, extrusion, in appropriate containers or in volumes each of which represents a therapeutical or treatment unit or an element of reaction, then again cooled to low temperature, most usually of the order of $-50°$ to $-70°$ C. in accordance with an appropriae cycle until the interstitial liquids have completely hardened.

A lyophilization is then carried out on the particles or volumes of the hardened frozen product, in accordance with a cycle adapted to each case.

Note that in some cases, the product may be divided up by acting either on the hardened frozen product or on the dry lyophilized product by appropriate mechanical means.

After drying, there are thus obtained stabilized products of very high porosity which may be employed as such or serve as a base for subsequent operations or be put back into solution or suspension in appropriate vehicles. Their high porosity and the evenness of their composition then impart thereto particularly remarkable properties among which is a very high dissolving rate.

Note that by operating on either of the aforementioned factors, such as the size of the microcrystals, it is possible to act on the porosity of the compositions obtained. Such a regulation can not be achieved by the use of the conventional technique of lyophilization. The process according to the invention permits the obtainment of a very homogeneous structure and in particular avoiding the formation of "crust" and "zoning".

In a modification of the process according to the invention, the procedure is as before but, before the operation for dividing or distributing the microcrystalline complex system, air or a neutral non-reactive gas under pressure is incorporated therein. This permits, at the moment of division or distribution, the expansion of the gas and imparts, at the end of the operation, to the dried product an even lacunary or cavitied structure of multiple applications. The density of the product thus obtained is a function of the pressure and nature of the gas admitted into the vessel.

In another modification of the process according to the invention, one or more more or less finely divided and cooled solid substances are incorporated into the microcrystalline complex system in the course of or immediately after the forming thereof.

Thus it is possible to add to the initial products substances which are insoluble or chemically incompatible with the initial products and/or with each other while ensuring their perfect dispersion within the mass. The following operations are carried out as before.

Thus, a cooled powder which is chemically incompatible with one or more products initially present may be incorporated in the microcrystalline complex system.

Solid products, crystals or other solid elements such as coated or encapsulated granules may also be added to the mass of the microcrystalline complex system.

The homogeneity of the mixture obtained permits a precise dosing of the added coated or uncoated elements in the remainder of the composition which thus serves as a dosing vehicle for these solid elements.

In another modification of the process according to the invention, an intimate mixture of chemically incompatible substances is produced by preparing them preferably in the form of microcrystalline complex systems as described previously and mixing them cold. The division or distribution of the mixture before or after hardening at low temperature is followed by freeze drying. In the course of the subsequent use of the products obtained, the reactive elements can combine and produce the desired effects.

This is the case of the cold mixing of an acid microcrystalline complex system and an alkaline microcrystalline complex system for the purpose of preparing lyophilized porous solids having effervescent properties when added to water.

In another modification of the process according to the invention, physically incompatible microcrystalline complex systems are mixed cold according to the mode of application described in the preceding paragraph.

It is thus possible to obtain the perfect mixture of an aqueous solution and an organic solution, or of two organic solutions in different solvents, which are individually lyophilizable, by intimately mixing their microcrystalline complexes, the rest of the procedure being as described before.

It is also possible to combine the preceding possibilities by effecting the intimate mixture of different compatible solutions, then converting them, according to the described process, into a microcrystalline complex system, then mixing two or several microcrystalline complex systems thus prepared, possibly with the addition of solid elements of various kinds and particle sizes, so as to obtain a homogeneous mass which is thereafter hardened by cooling and then lyophilized.

The following examples will illustrate the present invention.

EXAMPLE 1

The following solution is prepared:

Vincamine . . . 20 g
Lactose . . . 300 g
Polyvinylpyrrolidone . . . 50 g
Water to make up . . . 1000 g This solution is introduced in a stainless steel vessel provided with an agitator of variable speed and a nozzle placed in the bottom of the vessel which permits the controlled supply of a very fine current of liquid carbon dioxide gas.

Upon contact with the cold given off by the liquefied gas, there is a localized appearance of microcrystals of the solvent which are continuously put in suspension in the remaining liquid. The latter is progressively concentrated and there is finally obtained an intimate mixture of microcrystals of ice and highly-concentrated interstitial liquids forming a microcrystalline complex system which is viscous at a temperature of the order of $-15°$ C.

This complex is distributed in cold moulds which are immediately brought to a low temperature, about $-50°$ C., for 10 minutes.

The hardened moulded formulations are then conveyed to the lyophilizer.

After drying, there are obtained formulations of light solid product which are relatively friable and break up within 5 seconds in water.

EXAMPLE 2

The operation is carried out with the same solution and under the same conditions as in the Example 1, but by closing the vessel hermetically and controlling by means of a valve the escape of the carbon dioxide which has passed from the liquid state to the gaseous state. Before having reached the desired viscosity of the microcrystalline complex system, this valve is closed and the pressure of the gas rises to about 1 bar within the vessel.

When the lower valve of the vessel is opened for receiving the microcrystalline complex, the latter flows but the mixed gas, in escaping, produces an expansion which gives, after drying, a lacunary structure which imparts to the dry product an even higher dissolving rate.

EXAMPLE 3

A solution of 500 g of citric acid in 500 g of water is prepared. This solution is placed in a vessel provided with an agitator and, in its lower part, with a nozzle for the supply of liquefied cooling gas.

While agitating or stirring, liquid nitrogen is admitted in a controlled manner. In this way microcrystals of ice are formed which are continuously put back into suspension in the remaining liquid by agitation.

When the microcrystalline complex system has acquired the desired viscosity, there are added thereto, while mixing, 300 g of sodium acid carbonate which is finely powdered and cooled to $-25°$ C.

When the mixture has been achieved, it is distributed in cooled moulds which are thereafter brought to about $-50°$ C. for 10 minutes.

The hardened moulded formulations are thereafter placed in a lyophilizer.

The lyophilized formulations obtained are light, have a good mechanical behaviour and dissolve in water with effervescence in a practically instantaneous manner.

EXAMPLE 4

The three following solutions are prepared:

| A - Citric acid | 500 g |
| Water | 500 g |
| B - Sodium acid carbonate | 300 g |
| Water | 300 g |
| C - Acetyl/salicylic acid | 500 g |
| Dioxane | 500 g. |

Each of these solutions is placed in a vessel similar to that employed in Example 3 and cooled by the controlled injection of liquid nitrogen until each solution gives a microcrystalline complex, at a temperature of the order of $-15°$ C.

The three complexes are then mixed until homogeneity.

The final mixture is distributed in cold moulds which are thereafter brought to −50° C. for 10 minutes.

The hardened moulded formulations are thereafter lyophilized.

The dry products obtained are in the form of divisions of 1.3 g which are relatively friable and instantaneously soluble by yielding 500 mg of acetyl/salicylic acid in extremely fine particles.

EXAMPLE 5

The following solution is prepared:
Vincamine ... 5 g
Glycocoll ... 300 g
Polyvinylpyrrolidone ... 30 g
Water to make up ... 1000 g This solution is placed in a vessel having a frozen and scraped surface. The solution is cooled while agitating and scraping until a microcrystalline complex is obtained at the temperature of about −15° C.

15 g of Vincamine, in the form of microcapsules having a retarded liberation of Vincamine representing 50% by weight, namely 30 g of these microcapsules, are introduced into this complex.

The mixture of the microcapsules, of a mean diameter of 1 mm, with the microcrystalline complex is homogenized, then distributed in moulds, which are themselves cooled, in the proportion of 2 g of mixture per mould.

The moulded formulations are then brought to about −60° C. and then lyophilized.

The lyophilizates obtained correspond to 40 mg of Vincamine hydrochloride per unit. A quarter of the active principle is liberated at the moment of the dissolving of the lyophilizate and is therefore immediately available. The remaining three quarters, namely 30 mg, are in the form of microcapsules liberated in the liquid upon the dissolving of the lyophilizate. The microcapsules are absorbed at the same time as the solution but only progressively liberate the active principle they contain.

An examination of the lyophilizates has shown the very good distribution of the microcapsules in the remainder of the composition. This proves that it is thus possible to obtain a perfect distribution of the elements present in the composition which acts as a vehicle-dose.

Having now described my invention, what I claim as new and desire to secure by Letters Patent is:

1. A process for preparing pharmaceutical, cosmetic or diagnostic formulations by the freeze drying of at least one substance contained in at least one solvent, comprising locally and progressively cooling in a controlled manner while agitating the solvent containing said substance so as to produce microcrystals of solvent which are put in suspension in the remainder of the liquid until the obtainment of a high-viscosity microcrystalline complex system comprising essentially isolated microcrystals of solvent in intimate mixture with interstitial liquid phases having a high concentration of the initially present substance, hardening the microcrystalline complex system by cooling at a temperature of about −50° to −70° C. and then lyophilizing the hardened microcrystalline complex system.

2. The process claimed in claim 1, and preliminarily placing said substance in solution in said solvent.

3. The process claimed in claim 1, and preliminarily placing said substance in suspension in said solvent.

4. The process claimed in claim 1, and producing the microcrystalline complex system by progressively, locally and controlledly cooling with agitation in a vessel and injecting a cooling fluid into said vessel.

5. The process claimed in claim 1, and producing the microcrystalline complex system by a progressive, localized and controlled cooling while agitating in a vessel having a surface which is cooled and scraped.

6. The process claimed in claim 1, comprising incorporating a neutral gas in the microcrystalline complex system under pressure so as to obtain an expansion of the mass when the mass is subsequently divided up.

7. The process claimed in claim 1, comprising incorporating in the microcrystalline complex system at least one substantially finely divided solid substance.

8. The process claimed in claim 7, and effecting said incorporation of at least one substance in the course of the formation of the microcrystalline complex system.

9. The process claimed in claim 7, and effecting said incorporation of at least one substance immediately after the formation of the microcrystalline complex system.

10. The process claimed in claim 7, wherein said divided substance is a cooled powder which is chemically incompatible with at least one of the substances contained in the mass to be lyophilized before the cooling thereof.

11. The process claimed in claim 7, wherein said divided substance consists essentially of solid particles, the remainder of the composition acting as a vehicle-dose for said particles.

12. The process claimed in claim 7, wherein said divided substance consists essentially of crystals, the remainder of the composition acting as a vehicle-dose for said crystals.

13. The process claimed in claim 7, wherein said divided substance consists essentially of coated granules, the remainder of the composition acting as a vehicle-dose for said granules.

14. The process claimed in claim 1, and mixing the microcrystalline complex system cold with another microcrystalline complex system obtained by the same process.

15. The process claimed in claim 14, and obtaining the cold microcrystalline complex systems from solutions to be lyophilized which are chemically incompatible.

16. The process claimed in claim 14, and obtaining the cold microcrystalline complex systems from suspensions to be lyophilized which are chemically incompatible.

17. The process claimed in claim 14, and obtaining the cold microcrystalline complex systems from solutions to be lyophilized which are physically incompatible.

18. The process claimed in claim 14, and obtaining the cold microcrystalline complex systems from suspensions to be lyophilized which are physically incompatible.

19. The process claimed in claim 1, and dividing up the hardened frozen product by mechanical means.

20. The process claimed in claim 1, and dividing up the final dried product by mechanical means.

* * * * *